United States Patent [19]

Brannan et al.

[11] Patent Number: 5,366,498
[45] Date of Patent: Nov. 22, 1994

[54] DEVICE FOR TREATING FINE SUPERFICIAL FACIAL LINES

[75] Inventors: Ann Brannan, San Francisco; Roseann Burhenne, Los Altos Hills; Frank A. Delustro, Belmont; Thomas L. Smestad, Palo Alto; Louis Fries, Los Altos; Rees M. Orland, Los Altos Hills, all of Calif.

[73] Assignee: Collagen Corporation, Palo Alto, Calif.

[21] Appl. No.: 16,490

[22] Filed: Feb. 10, 1993

Related U.S. Application Data

[63] Continuation of Ser. No. 677,403, Mar. 29, 1991, abandoned.

[51] Int. Cl.$^5$ ............................................. A61F 2/10
[52] U.S. Cl. ...................................... 623/11; 623/66
[58] Field of Search .................. 623/15, 11; 604/187, 604/243; 128/DIG. 8

[56] References Cited

U.S. PATENT DOCUMENTS

| | | | |
|---|---|---|---|
| 3,949,073 | 4/1976 | Daniels et al. | 424/177 |
| 4,424,208 | 1/1984 | Wallace et al. | 424/177 |
| 4,488,911 | 12/1984 | Luck et al. | 106/161 |
| 4,582,640 | 4/1986 | Smestad et al. | 128/DIG. 8 X |
| 4,642,117 | 2/1987 | Nguyen et al. | 623/15 X |

OTHER PUBLICATIONS

Sherwood Medical Catalog–Apr. 5, 1989 p. 4 under Needles & Syringe Section.

*Primary Examiner*—David Isabella
*Attorney, Agent, or Firm*—Morrison & Foerster

[57] ABSTRACT

A device for correcting fine superficial facial lines which comprises a syringe fitted with a 31–33 gauge needle and an aqueous suspension of noncrosslinked fibrillar atelopeptide collagen contained within the syringe barrel, the concentration of collagen in the suspension being in the range of 10 to 50 mg/ml and the suspension exhibiting an extrusion plot in which there is a smooth substantially linear increase in force up to a substantially constant force in the range of 5 to 30 newtons.

6 Claims, No Drawings

DEVICE FOR TREATING FINE SUPERFICIAL FACIAL LINES

This application is a continuation of application Ser. No. 07/677,403, filed Mar. 29, 1991, now abandoned.

TECHNICAL FIELD

This invention is in the field of plastic surgery/dermatology and relates specifically to correcting fine superficial facial lines such as those around the eyes by injecting aqueous suspensions of particulate biomaterials, such as collagen, intradermally at the site of the lines.

BACKGROUND

Injectable forms of purified atelopeptide collagen have been commercially available for many years for soft tissue augmentation. Daniels et al., U.S. Pat. No. 3,949,073, initiated the development of these materials. They describe an injectable solution of atelopeptide which when injected forms a fibrillar collagen implant. Forms of this material are now commercially available from Collagen Corporation (Palo Alto, Calif.) under the trademark ZYDERM®. ZYDERM® collagen implant is prepackaged in a one cc syringe (Medical Molding Co. of America) fitted with a 30 gauge needle.

U.S. Pat. No. 4,488,911 assigned to Collagen Corporation describe a method for preparing purified atelopeptide collagen in solution (CIS). Native collagen, typically of bovine origin, is extracted from tissue in dilute aqueous acid and then digested with a protease such as pepsin, trypsin or PRONASE® to remove the telopeptides from the ends of the collagen molecules. Atelopeptide collagen fibers may be reconstituted from CIS by raising the pH of the solution.

U.S. Pat. No. 4,582,640, also assigned to Collagen Corporation, describes a crosslinked form of atelopeptide fibrillar collagen. An injectable suspension of this crosslinked material is available commercially from Collagen Corporation under the trademark ZYPLAST®. This product is prepackaged in a syringe in the same manner as the ZYDERM® product.

U.S. Pat. No. 4,642,117, also assigned to Collagen Corporation, describes a method for reducing the viscosity of reconstituted CIS by passing the reconstituted fibers through a fine mesh screen.

ZYDERM® and ZYPLAST® collagen implants have enjoyed great commercial success and are used to treat a large variety of soft tissue anomalies. However, physicians have found one type of skin contour, fine superficial facial lines, particularly those about the eyes, (i.e., crows' feet) difficult to treat with these products. Specifically, physicians questioned about such treatment indicated inter alia that (1) they had negative experiences in using prior products due to lumpiness or beading of the injectate, (2) the nature of the skin surrounding the eye increased the possibility of the injection causing trauma or bruising of the area and (3) the treatment required greater control or precision than that which is achievable with these prior products.

Applicants addressed these shortcomings and found that a greatly improved product for treating fine superficial facial lines was achievable through a combination of modifying both the syringe and the injectate.

DISCLOSURE OF THE INVENTION

Accordingly, one aspect of the present invention is a method for correcting fine superficial facial lines comprising injecting an aqueous suspension of a particulate biomaterial at a concentration of 10 to 50 mg/ml wherein the suspension displays an extrusion plot in which there is a smooth substantially linear increase in force up to a substantially constant force in the range of 5 to 30 newtons intradermally at the site of the lines from a syringe having a 31 to 33 gauge needle.

Another aspect of the invention is a device for use in correcting fine superficial facial lines comprising:

(a) a syringe having a barrel fitted with a fine gauge needle, the needle having a gauge in the range of 31 and 33 inclusive;

(b) an aqueous suspension of a particulate biomaterial contained within the barrel, particulate biomaterial having a concentration in the suspension being in the range of 10 to 50 mg/ml, the particulate biomaterial further being comprised of fibrils of uniform size whereby the uniform size of the fibrils results in improved flow characteristics and enhanced extrudability of the suspension through the fine gauge needle such that the suspension displays an extrusion plot in which there is a smooth substantially linear increase in force up to a substantially constant force in the range of 5 to 30 newtons.

MODES FOR CARRYING OUT THE INVENTION

A. Definitions

The term "atelopeptide" collagen refers to collagen which has been treated to remove the immunogenic terminal portions. Typically, collagen is treated with acid to swell the fibers, and the swollen fibers digested with a suitable protease (e.g., trypsin) to remove the terminal portions. The product is soluble in acidic solutions (e.g., about pH 2.0).

The term "reconstituted atelopeptide collagen" refers to uncrosslinked collagen which has been precipitated into a fibrillar form somewhat resembling the triple-helical form of collagen in its natural state. Thus, reconstituted atelopeptide collagen morphologically resembles native collagen, but omits the immunogenic telopeptide regions of the protein.

The term "precipitated" fibrillar atelopeptide collagen refers to uncrosslinked collagen which has been reconstituted into fibrillar form by precipitation from acidic solution.

The phrase "fine superficial facial lines" intends shallow linear depressions in the facial skin that are typically associated with aging or repeated flexing of the skin. They are most commonly found in crow's feet (at the outer edges of the eyes), vertical lines above the upper lips, and around the mouth.

The term "particulate" biomaterial intends materials that are particulate in form (e.g., fibrous or nonfibrous bodies) that are medically acceptable for implantation within humans for augmenting soft tissue. Examples of biomaterials that have been used or proposed for such use are fibrillar noncrosslinked atelopeptide collagen, crosslinked fibrillar atelopeptide collagen, gelatin beads, beads of natural or synthetic polymers such as polytetrafluoroethylene (TEFLON® polymer), silicone rubber, and various hydrogels such as polyacrylonitrile-polyacrylamide hydrogels. Fibrillar noncrosslinked atelopeptide collagen is a preferred biomaterial and is used as an exemplary material in the following disclosure.

The term "extrusion plot" refers to a graph of syringe plunger travel in cm versus force in newtons applied to the plunger obtained by loading a test aqueous suspension of particulate biomaterial in a 1.25 cc Burron syringe fitted with a 32 gauge needle and applying such force as to give a constant plunger displacement rate of 30 mm/min. Suspensions that may be used in the invention exhibit an extrusion plot in which there is a smooth (i.e. substantially free of spikes or transient increases (see U.S. Pat. No. 4,642,117)) linear increase or ramp up in force from zero force to a substantially constant force (i.e. a plateau) in the range of 5 to 30 newtons.

B. Collagen Suspension

The collagen suspension that may be employed as a particulate biomaterial in the invention is made from sterile CIS. For example, one may use VITROGEN ® 100 collagen-in-solution (CIS), which is commercially available from Celtrix Pharmaceuticals, Inc. Palo Alto, Calif., and is a sterile solution containing 3 mg/ml atelopeptide bovine hide collagen in a pH 2 buffer. Alternatively, one may prepare CIS by methods known in the art. In general, cowhide is dehaired, ground, and soaked in acid (e.g., aqueous HCl) to swell the collagen fibers. The product is then treated with a suitable protease (other than collagenase) such as pepsin or trypsin, and then sterile filtered.

Fibrillar atelopeptide collagen (also referred to as "reconstituted" collagen) is prepared from CIS by raising the pH to about 7.4 by adding a sufficient quantity of a $Na_2PO_4$ buffer, thus precipitating the fibers from solution. The concentration of collagen in the resulting suspension is about 3 mg/ml. The suspension is then passed continuously through a 50 mesh (0.013 in. openings) screen until it has passed 90 times through the screen (flow rate and time depend on the volume of suspension and diameter of the screen) and concentrated by centrifugation to about 70 mg/ml. The screening breaks up large fibrils, making the fiber size more uniform. This results in improved flow characteristics providing enhanced extrudability for fine gauge needles and improved intrudability into the skin. The concentrate is then homogenized with phosphate-buffered saline (optionally including an anesthetic agent such as Lidocaine) to a concentration of 10 to 50 mg/ml, preferably 30–40 mg/ml, and then loaded into the syringe.

C. Syringes

The syringes used in this invention comprise a barrel, a plunger received in the barrel, and a fine gauge needle attached to the leading end of the barrel via an appropriate fitting such as a Luer lock fitting. Burron syringes with a 4 to 10 mm I.D. diameter barrel 4 to 8 mm long are preferred because of their smallness and compactness. The fine gauge needle is 31-33 gauge of about 0.90 to 1.3 cm in length (e.g., approximately ⅜ to ½ inch). The needle is typically made from stainless steel and is presterilized. The use of such a fine gauge needle reduces or eliminates trauma/bruising at the treatment site, provides more control (precision) in the injection, and is less intimidating to some patients.

Clinical experience indicated that a volume of approximately 0.7 cc of collagen suspension is optimal to achieve full correction of fine lines in a first treatment. In some instances, a following "touch-up" injection may be needed. Such treatments require less volume, typically on the order of about 0.4 cc.

Quantitative confirmation of the flow characteristics of the suspension may be carried out by running extrusion tests on samples of the loaded syringes as follows. The loaded syringes are refrigerated at 2°–10° C. for 12 hours prior to testing. They are allowed to warm at room temperature for 5 minutes prior to testing. The sample syringe is placed on an extrusion test device similar to an Instron machine. The device is adapted to plunge the plunger at a constant rate of travel (linear displacement), measure the force applied to the plunger during its travel, and plot the force versus plunger travel on a chart recorder. As indicated above, at a linear plunger displacement of 30 mm/min the plot should appear as a smooth linear ramp up in force from zero force to a constant force plateau of 5 to 30 newtons in magnitude, preferably 10 to 30 newtons with an average of about 25 newtons.

D. Administration

The region of fine superficial facial lines is located and preferably placed under magnification. The tissue at the site is then stretched to give a taut surface. The needle is then inserted into the skin site as superficially as possible. The position of the needle bevel (up or down) is dictated by physician preference—the objective being to achieve superficial placement of the injectate.

The suspension is then injected using a steady pressure on the syringe plunger until a slight blanch occurs. Multiple serial punctures in the area are advisable. When injecting into a periorbital region care should be taken to not overcorrect (inject excessive volume of suspension).

CLINICAL RESULTS

A blind study was conducted to compare treatment of fine superficial facial lines using commercially available ZYDERM ® I collagen implant (Collagen Corp.) (this product had a 1 cc syringe fitted with a 30 gauge needle and the collagen was not screened) and devices made according to this invention (1.25 cc Burron syringes, 32 gauge needle loaded with reconstituted atelopeptide collagen having an extrusion plot as described above. The collagen concentration was 35 mg/ml in both projects.

The study involved 103 patients who were treated with unmarked invention devices in the periorbital area on one side and with unmarked ZYDERM ® I product on the other side. Neither physicians nor patients knew which material was used. The results of the comparison showed significantly less post-treatment trauma experienced with the invention, with most investigators preferring the invention device over the ZYDERM ® I product. Many investigators reported less lumping and beading of injected material with the invention than with the ZYDERM ® I product. Interviews with investigators also showed there was a perception (not supported by clinical data) that the invention device was less painful than the ZYDERM ® I product.

Modifications of the above-described modes for carrying out the invention that are obvious to those of skill in the fields of medical devices, injectables, and biomaterial formulation are intended to be within the scope of the following claims.

We claim:

1. A device for use in correcting fine superficial facial lines comprising:
   (a) a syringe having a barrel fitted with a fine gauge needle, the needle having a gauge in the range from 31 to 33, inclusive,
   (b) an aqueous suspension of fibrillar noncrosslinked atelopeptide collagen contained within the barrel, the collagen having a concentration in the suspension in the range of 10 to 50 mg/ml, the collagen further being comprised of fibrils of uniform size whereby the uniform size of the fibrils results in improved flow characteristics and enhanced extrudability of the suspension through the fine gauge needle such that the suspension exhibits an extrusion plot in which there is a smooth substantially linear increase in force up to a substantially constant force in the range of 10 to 30 newtons with an average of about 25 newtons.

2. The device of claim 1 wherein said collagen concentration is 30 to 40 mg/ml.

3. The device of claim 1 wherein the needle gauge is 32.

4. The device of claim 2 wherein the needle gauge is 32.

5. The device of claim 4 wherein the barrel has an inner diameter of 4 to 10 mm and the volume of suspension in the barrel is 0.4 to 0.7 cc, inclusive.

6. The device of claim 1 wherein said uniform size fibrils are formed by passing the collagen through a 50 mesh screen.

* * * * *